US00PP14660P29

(12) United States Plant Patent

Hofmann et al.

(10) Patent No.: US PP14,660 P2
(45) Date of Patent: Mar. 30, 2004

(54) NEMESIA PLANT NAMED 'INNKAPINK'

(50) Latin Name: *Nemesia hybrid*
Varietal Denomination: Innkapink

(76) Inventors: Silvia Hofmann, Engel Strasse 72, 55124 Mainz (DE); Susanne Herdegen, Am Dreschacker 41, D-55278 Dexheim (DE)

( * ) Notice: Subject to any disclaimer, the term of this patent is extended or adjusted under 35 U.S.C. 154(b) by 0 days.

(21) Appl. No.: 10/385,254

(22) Filed: Mar. 10, 2003

(51) Int. Cl.[7] ..... A01H 5/00
(52) U.S. Cl. ..... Plt./263
(58) Field of Search ..... Plt./263

(56) References Cited

U.S. PATENT DOCUMENTS

PP12,608 P2 * 5/2002 Hammett ..... Plt./263
PP13,229 P2 * 11/2002 Hammett ..... Plt./263
PP13,380 P2 * 12/2002 Hammett ..... Plt./263
2003/0126658 P1 * 7/2003 Jones ..... Plt./263

OTHER PUBLICATIONS

UPOV ROM GTITM Computer Database, GTI Jouve Retrieval Software 2003/04 Citation(s) for 'Innkapink'.* wysiwyg://9/http://www.engo.sk/default.php?iddata=216.* http://www.fleischle.de/Nemesia/Nemesia%20Karoo/nemesia.htm.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Nemesia plant named 'Innkapink', characterized by its upright plant habit; freely branching habit; and numerous light purple-colored flowers that are fragrant.

1 Drawing Sheet

Botanical classification/cultivar designation: Nemesia hybrid cultivar Innkapink.

BACKGROUND OF THE INVENTION

The present invention relates to a new and distinct cultivar of Nemesia plant, botanically known as Nemesia hybrid and referred to by the name 'Innkapink'.

The new Nemesia is a product of a planned breeding program conducted by the Inventors in Gensingen, Germany. The objective of the program is to create new compact Nemesia cultivars with numerous flowers, unique flower colors and fragrance.

The new Nemesia originated from a cross by the Inventors of a proprietary Nemesia hybrid selection identified as code NJ99-1, not patented, as the female, or seed, parent with a proprietary Nemesia hybrid selection identified as code N98Sa5-C, not patented, as the male, or pollen, parent during the summer of 1999. The cultivar Innkapink was discovered and selected by the Inventors as a flowering plant within the progeny of the stated cross in a controlled environment in Gensingen, Germany during the summer of 1999.

Asexual reproduction of the new Nemesia by terminal cuttings taken in a controlled environment in Gensingen, Germany since 1999, has shown that the unique features of this new Nemesia are stable and are reproduced true to type in successive generations.

SUMMARY OF THE INVENTION

The new Nemesia has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Innkapink' and distinguish 'Innkapink' as a new and distinct cultivar:

1. Upright plant habit.
2. Freely branching habit.
3. Numerous light purple-colored flowers that are fragrant.

Plants of the new Nemesia differ primarily from plants of the female parent selection in the following characteristics:

1. Plants of the new Nemesia flower earlier than plants of the female parent selection.
2. Plants of the new Nemesia have larger flowers than plants of the female parent selection.
3. Plants of the new Nemesia are more freely flowering than plants of the female parent selection.

Plants of the new Nemesia differ primarily from plants of the male parent selection in the following characteristics:

1. Plants of the new Nemesia are more vigorous than plants of the male parent selection.
2. Plants of the new Nemesia have a more uniform plant habit than plants of the male parent selection.
3. Flowers of plants of the new Nemesia are more fragrant than flowers of plants of the male parent selection.

Plants of the new Nemesia can be compared to plants of the cultivar Melanie, not patented. In side-by-side comparisons conducted in Gensingen, Germany, plants of the new Nemesia differed from plants of the cultivar Melanie in the following characteristics:

1. Plants of the new Nemesia were more vigorous than plants of the cultivar Melanie.
2. Plants of the new Nemesia had larger flowers than plants of the cultivar Melanie.

3. Plants of the new Nemesia had lighter colored flowers than plants of the cultivar Melanie.

BRIEF DESCRIPTION OF THE PHOTOGRAPHS

The accompanying colored photographs illustrate the overall appearance of the new Nemesia, showing the colors as true as it is reasonably possible to obtain in colored reproductions of this type. Colors in the photographs may differ slightly from the color values cited in the detailed botanical description which accurately describe the colors of the new Nemesia.

The photograph at the top of the sheet comprises a side perspective view of a typical potted plant of 'Innkapink' that was about four weeks old.

The photograph at the bottom of the sheet comprises a close-up view of typical flowers of 'Innkapink'.

DETAILED BOTANICAL DESCRIPTION

The aforementioned photographs and following observations and averaged measurements describe plants grown in Bonsall, Calif., in an outdoor nursery during the spring with day temperatures ranging from 18 to 35° C. and night temperatures ranging from 7 to 18° C. After rooting, plants were grown for four weeks in 15-cm containers with three plants per container. Color references are made to The Royal Horticultural Society Colour Chart, 1995 Edition, except where general terms of ordinary dictionary significance are used.

Botanical classification: Nemesia hybrid cultivar Innkapink.

Parentage:

*Female parent.*—Proprietary Nemesia hybrid selection identified as code NJ00-1, not patented.

*Male parent.*—Proprietary Nemesia hybrid selection identified as code N98Sa-C, not patented.

Propagation:

*Type.*—By vegetative cuttings.

*Time to initiate roots.*—About 10 to 14 days at 20° C.

*Time to develop roots.*—About two to three weeks at 20° C.

*Root description.*—Fibrous, fine; white in color.

Plant description:

*General appearance.*—Upright plant habit; inverted triangle. Freely branching, typically about six primary lateral branches and about six secondary lateral branches. Numerous light purple-colored zygomorphic flowers. Vigorous growth habit.

*Plant height.*—About 30 cm.

*Plant diameter or spread.*—About 26 cm.

*Lateral branches.*—Appearance: Square in cross-section with longitudinal ridges. Length: About 27 cm. Diameter: About 4 mm. Internode length: About 3.5 to 4.5 cm. Strength: Strong. Texture: Glabrous. Color: 144B.

*Foliage description.*—Arrangement: Opposite, simple. Shape: Elliptic to lanceolate. Apex: Broadly acute. Base: Attenuate. Length: About 4.7 cm. Width: About 2.4 cm. Margin: Serrate. Texture, upper and lower surfaces: Glabrous. Venation pattern: Pinnate, arcuate. Petiole length: About 6 mm. Petiole diameter: About 3 mm. Color: Developing and fully expanded leaves, upper surface: 147A. Developing and fully expanded leaves, lower surface: 147B. Venation, upper and lower surfaces: 147B. Petiole: 144B.

Flowering description:

*Arrangement/appearance.*—Zygomorphic solitary flowers arranged on terminal racemes; flowering acropetally towards apex. Flowers bilabiate with nectar spur. Flowers face outward. Flowers last about four to five days on the plant. Flowers not persistent.

*Natural flowering season.*—Natural flowering season is spring to fall; flowering continuous during this period.

*Quantity of flowers.*—Freely flowering with about 17 to 20 flowers and flower buds per raceme at one time.

*Fragrance.*—Floral-like.

*Inflorescence length.*—About 10 cm.

*Inflorescence diameter.*—About 3.5 cm.

*Flower diameter.*—About 2 cm by 1.8 cm.

*Flower depth, including nectar spur.*—About 2.5 cm.

*Flower buds.*—Shape: Ovoid with spur. Length including spur: About 1.2 cm. Diameter: About 8 mm. Color: Lighter than 69D.

*Petals.*—Arrangement/shape: Five petals total. Four upper petals are fused at base to form an upright lobed and arched banner lip; lower petal modified into a larger lip with nectar spur and convex oval protuberance which serves as pollinator nectar guide and landing platform. Apex: Rounded. Margin: Entire. Length: Upper lip petals: About 1 cm. Lower lip petal: About 7 mm. Width: Upper lip petals: About 5 mm. Lower lip petal: About 1.4 cm. Texture: Smooth, velvety. Color: When opening, upper surface: 76D. When opening, lower surface: More white than 76D. Fully opened, upper surface: 82C; towards base, 157C; color becoming closer to lighter than 85D with development. Fully opened, lower surface: 75D. Nectar guide: 7A. Nectar spur: Close to 75D.

*Sepals.*—Quantity: Five-parted, star-shaped calyx. Shape: Elliptic. Apex: Acute. Base: Fused. Margin: Entire. Length: About 4 mm. Diameter: About 2 mm. Texture, upper and lower surfaces: Pubescent. Color, upper and lower surfaces: 147B.

*Peduncle.*—Length: About 6.5 cm. Diameter: About 2 mm. Strength: Strong. Angle: Upright to 45° from the stem. Color: 144A.

*Pedicel.*—Length: About 7.5 mm. Diameter: About 1 mm. Strength: Slender, but hold flowers outward. Angle: About 45° from the stem. Color: 144A.

*Androecium.*—Stamen number: Four per flower. Anther shape: Oval. Anther size: Less than 1 mm. Anther color: 7A. Amount of pollen: Scarce. Pollen color: 7A.

*Gynoecium.*—Pistil number: One per flower. Pistil length: About 3 mm. Style length: About 1.5 mm. Style color: 145C. Stigma shape: Rounded. Stigma color: 145C. Ovary color: 145A.

*Seed/fruit.*—Seed and fruit production has not been observed on plants of the new Nemesia.

Disease/pest resistance: Plants of the new Nemesia have not been observed to be resistant to pathogens or pests common to Nemesias.

Temperature tolerance:

Plants of the new Nemesia have been observed to be tolerant to temperatures ranging from 0° to 38° C.

It is claimed:

1. A new and distinct cultivar of Nemesia plant named 'Innkapink', as illustrated and described.

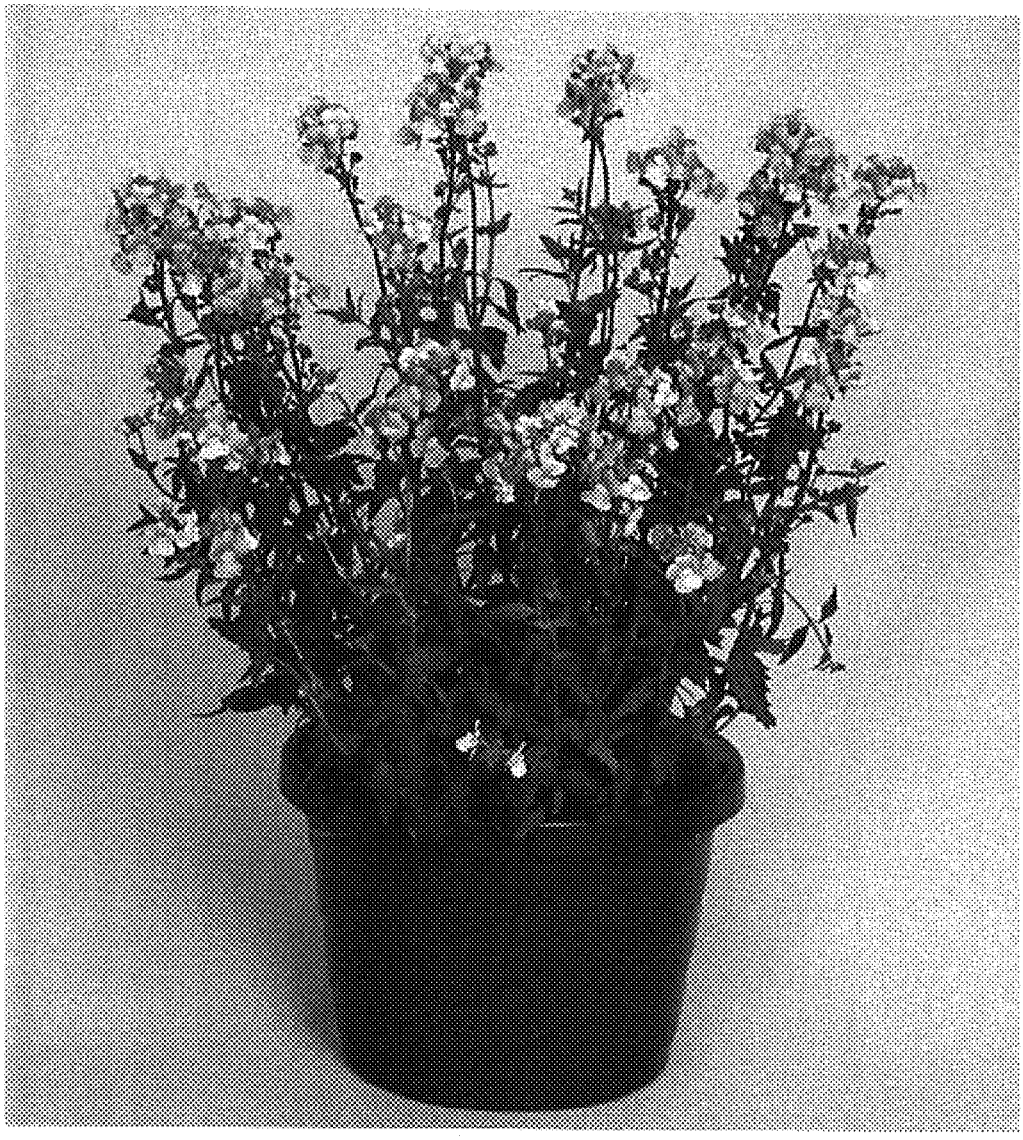
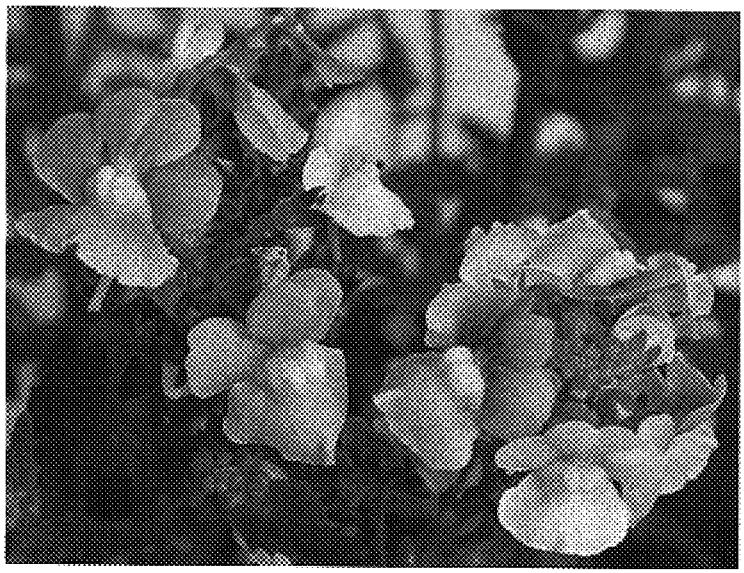

* * * * *